(12) United States Patent
Cutting et al.

(10) Patent No.: US 9,301,520 B2
(45) Date of Patent: Apr. 5, 2016

(54) SYSTEMS AND METHODS FOR FREEZING, STORING AND THAWING BIOPHARMACEUTICAL MATERIALS

(75) Inventors: Jonathan Cutting, Fairfield, CA (US); Isabelle Gay, Peypin (FR); Eric K. Lee, Acton, MA (US); Nicolas Voute, Cuges les Pins (FR)

(73) Assignee: SARTORIUS STEDIM NORTH AMERICA INC., Bohemia, NY (US)

(*) Notice: Subject to any disclaimer, the term of this patent is extended or adjusted under 35 U.S.C. 154(b) by 1502 days.

(21) Appl. No.: 11/963,106

(22) Filed: Dec. 21, 2007

(65) Prior Publication Data

US 2009/0158755 A1      Jun. 25, 2009

(51) Int. Cl.
  *B65D 1/32*       (2006.01)
  *A01N 1/02*       (2006.01)
  *F25C 1/22*       (2006.01)

(52) U.S. Cl.
  CPC .............. *A01N 1/0263* (2013.01); *A01N 1/02* (2013.01); *F25C 1/22* (2013.01); *Y10T 29/53443* (2015.01)

(58) Field of Classification Search
  USPC .............. 220/723, 592.15, 4.24, 23.91, 4.07, 220/495.05, 495.06; 206/508, 511, 505; 62/457.1, 66
  See application file for complete search history.

(56) References Cited

U.S. PATENT DOCUMENTS

| | | | |
|---|---|---|---|
| 2,633,006 A | 3/1953 | Taylor | |
| 2,722,111 A | 11/1955 | Taylor | |
| 2,794,570 A | 6/1957 | Downs | |
| 3,133,677 A | 5/1964 | Bertels | |
| 3,244,311 A | 4/1966 | Lawson | |
| 3,265,254 A | 8/1966 | Carter et al. | |
| 3,586,097 A | 6/1971 | Bender et al. | |
| 3,875,754 A | 4/1975 | Faust et al. | |
| 3,986,506 A | 10/1976 | Garber et al. | |

(Continued)

FOREIGN PATENT DOCUMENTS

DE    3142521     11/1987
DE    4308383 A1   3/1993

(Continued)

OTHER PUBLICATIONS

International Search Report for corresponding International Application No. PCT/US2008/087728, filed Dec. 19, 2008, completed on Feb. 11, 2010, and mailed on Mar. 3, 2010.

(Continued)

*Primary Examiner* — Jeffrey Allen
(74) *Attorney, Agent, or Firm* — Heslin Rothenberg Farley & Mesiti P.C.; Nicholas Mesiti, Esq.; Victor A. Cardona, Esq.

(57) ABSTRACT

A system for using freezing, storing and thawing biopharmaceutical materials which includes a holder and a container for holding biopharmaceutical materials therein. The holder has a cavity and the container is received in the cavity. The holder includes a first portion and second portion. The container is received between the first portion and the second portion to connect the container to the holder. The holder includes an interior cradle having a bottom and edges extending from the bottom. The cradle bounds the cavity. An outer rim is connected to the cradle and separated from the cavity. The bottom includes an inner surface facing the cavity receiving the container and an outer surface. The outer surface of the bottom is recessed relative to an outer surface of the outer rim.

26 Claims, 13 Drawing Sheets

(56) References Cited

U.S. PATENT DOCUMENTS

| | | |
|---|---|---|
| 4,018,911 A | 4/1977 | Lionetti et al. |
| 4,079,529 A * | 3/1978 | Jennen et al. ............... 38/102.2 |
| 4,211,267 A | 7/1980 | Skovgaard |
| 4,251,995 A | 2/1981 | Pert et al. |
| 4,315,409 A | 2/1982 | Prentice et al. |
| 4,317,665 A | 3/1982 | Prentice |
| 4,327,799 A | 5/1982 | Scheiwe et al. |
| 4,365,629 A | 12/1982 | Pert et al. |
| 4,460,365 A | 7/1984 | Ganshirt et al. |
| 4,470,264 A | 9/1984 | Morris |
| 4,474,016 A | 10/1984 | Winchell |
| 4,482,585 A | 11/1984 | Ohodaira et al. |
| 4,491,225 A * | 1/1985 | Baillod ........................ 206/583 |
| 4,565,073 A | 1/1986 | Lavender |
| 4,783,042 A | 11/1988 | Folkmar |
| 4,811,465 A | 3/1989 | Folkmar |
| 4,869,398 A | 9/1989 | Colvin et al. |
| 4,903,827 A * | 2/1990 | Phelps et al. .................. 206/204 |
| 4,982,858 A * | 1/1991 | von Holdt .................... 220/23.4 |
| 4,993,579 A | 2/1991 | Burchett |
| 4,994,021 A | 2/1991 | Smith et al. |
| 5,168,725 A | 12/1992 | Margolin |
| 5,181,394 A | 1/1993 | Schea, III et al. |
| 5,197,601 A | 3/1993 | Sterett |
| 5,249,684 A | 10/1993 | Sterett |
| 5,250,044 A | 10/1993 | Irr et al. |
| 5,309,723 A | 5/1994 | Thomas et al. |
| 5,332,114 A | 7/1994 | Sano et al. |
| 5,361,906 A | 11/1994 | Sterett |
| 5,364,385 A | 11/1994 | Harms et al. |
| 5,390,791 A | 2/1995 | Yeager |
| 5,397,022 A * | 3/1995 | Schafer ........................ 220/675 |
| 5,405,000 A * | 4/1995 | Hagedon et al. ............. 206/216 |
| 5,431,496 A | 7/1995 | Balteau et al. |
| 5,435,142 A | 7/1995 | Silber |
| 5,465,865 A | 11/1995 | Coombes |
| 5,507,904 A | 4/1996 | Fisher et al. |
| 5,560,403 A | 10/1996 | Balteau et al. |
| 5,564,279 A | 10/1996 | Thomas et al. |
| 5,613,622 A | 3/1997 | Surrena et al. |
| D385,943 S | 11/1997 | Voelker |
| 5,756,193 A | 5/1998 | Yamamoto et al. |
| 5,769,235 A * | 6/1998 | Keach et al. ................. 206/583 |
| 5,863,715 A | 1/1999 | Rajotte et al. |
| 5,935,848 A | 8/1999 | Sputtek et al. |
| 5,988,422 A | 11/1999 | Vallot |
| 5,996,427 A * | 12/1999 | Masek et al. ................ 73/864.91 |
| 6,076,457 A | 6/2000 | Vallot |
| 6,146,124 A | 11/2000 | Coelho et al. |
| 6,186,932 B1 | 2/2001 | Vallot |
| 6,232,115 B1 | 5/2001 | Coelho et al. |
| 6,298,991 B1 | 10/2001 | Tsai |
| 6,302,327 B1 | 10/2001 | Coelho et al. |
| 6,371,643 B2 | 4/2002 | Saad et al. |
| 6,378,314 B1 | 4/2002 | Clark |
| 6,453,683 B1 | 9/2002 | Wisniewski et al. |
| 6,517,526 B1 | 2/2003 | Tamari |
| 6,550,966 B1 | 4/2003 | Saad et al. |
| 6,619,481 B2 * | 9/2003 | Merrell et al. ............... 206/721 |
| 6,631,616 B2 | 10/2003 | Wisniewski et al. |
| 6,635,414 B2 | 10/2003 | Wisniewski |
| 6,659,132 B2 | 12/2003 | Smith et al. |
| 6,670,175 B2 | 12/2003 | Wang et al. |
| 6,684,646 B2 | 2/2004 | Voute et al. |
| 6,698,213 B2 | 3/2004 | Voute et al. |
| 6,729,369 B2 | 5/2004 | Neas et al. |
| 6,764,482 B2 | 7/2004 | Keilman et al. |
| 6,769,231 B2 | 8/2004 | Danby |
| 6,786,054 B2 | 9/2004 | Voute et al. |
| 6,808,675 B1 | 10/2004 | Coelho et al. |
| 6,889,839 B1 * | 5/2005 | Rosten et al. ................. 206/583 |
| 6,945,056 B2 | 9/2005 | Brown et al. |
| 6,996,995 B2 | 2/2006 | Voute et al. |
| 7,137,261 B2 | 11/2006 | Brown et al. |
| 7,225,949 B2 | 6/2007 | Kubo et al. |
| 2001/0043763 A1 | 11/2001 | Saad et al. |
| 2002/0121527 A1 | 9/2002 | Good |
| 2003/0017066 A1 | 1/2003 | Danby et al. |
| 2003/0198406 A1 | 10/2003 | Bibbo et al. |
| 2004/0031273 A1 | 2/2004 | Lanctot |
| 2004/0096126 A1 | 5/2004 | Danby et al. |
| 2004/0107150 A1 | 6/2004 | Neas et al. |
| 2004/0144799 A1 | 7/2004 | Danby et al. |
| 2004/0144800 A1 | 7/2004 | Danby et al. |
| 2004/0221897 A1 | 11/2004 | Schubmehl et al. |
| 2004/0254560 A1 | 12/2004 | Coelho et al. |
| 2005/0183976 A1 | 8/2005 | Brothers |
| 2006/0112717 A1 | 6/2006 | Walton |
| 2006/0237341 A1 * | 10/2006 | McDade ....................... 206/509 |
| 2007/0084222 A1 | 4/2007 | Voute et al. |
| 2007/0125098 A1 | 6/2007 | Voute et al. |
| 2007/0209960 A1 * | 9/2007 | Leoncavallo et al. ......... 206/509 |
| 2007/0240432 A1 | 10/2007 | Voute et al. |

FOREIGN PATENT DOCUMENTS

| | | |
|---|---|---|
| DE | 44 33 147 A1 | 3/1996 |
| DE | 29703691 U1 | 3/1997 |
| DE | 100 03 102 A1 | 1/2002 |
| EP | 0 718 212 A1 | 6/1996 |
| EP | 1 112 946 A1 | 7/2001 |
| EP | 1 302 410 A1 | 4/2003 |
| FR | 2449429 | 2/1980 |
| FR | 2 887 335 A1 | 12/2006 |
| GB | 2046081 A | 2/1979 |
| JP | 54111998 | 9/1979 |
| JP | 2003205016 | 7/2003 |
| JP | 2005193013 | 7/2005 |
| WO | WO 9009184 | 1/1990 |
| WO | WO 92/00881 | 1/1992 |
| WO | WO 9623703 | 8/1996 |
| WO | WO 02092462 | 11/2002 |
| WO | WO 03/037082 A1 | 5/2003 |
| WO | WO 03/086269 A1 | 10/2003 |
| WO | WO 2007104047 A2 | 9/2007 |

OTHER PUBLICATIONS

Written Opinion of the International Searching Authority for corresponding International Application No. PCT/US2008/087728, filed Dec. 19, 2008, completed on Feb. 11, 2010, and mailed on Mar. 3, 2010.

Delta T (Pharma Logistic): "Total Temperature Security—Catalogue 2006", Internet Citation, Apr. 27, 2006; XP002567985, retrieved from the Internet: URL:http://www.deltat.de/home.html.

* cited by examiner

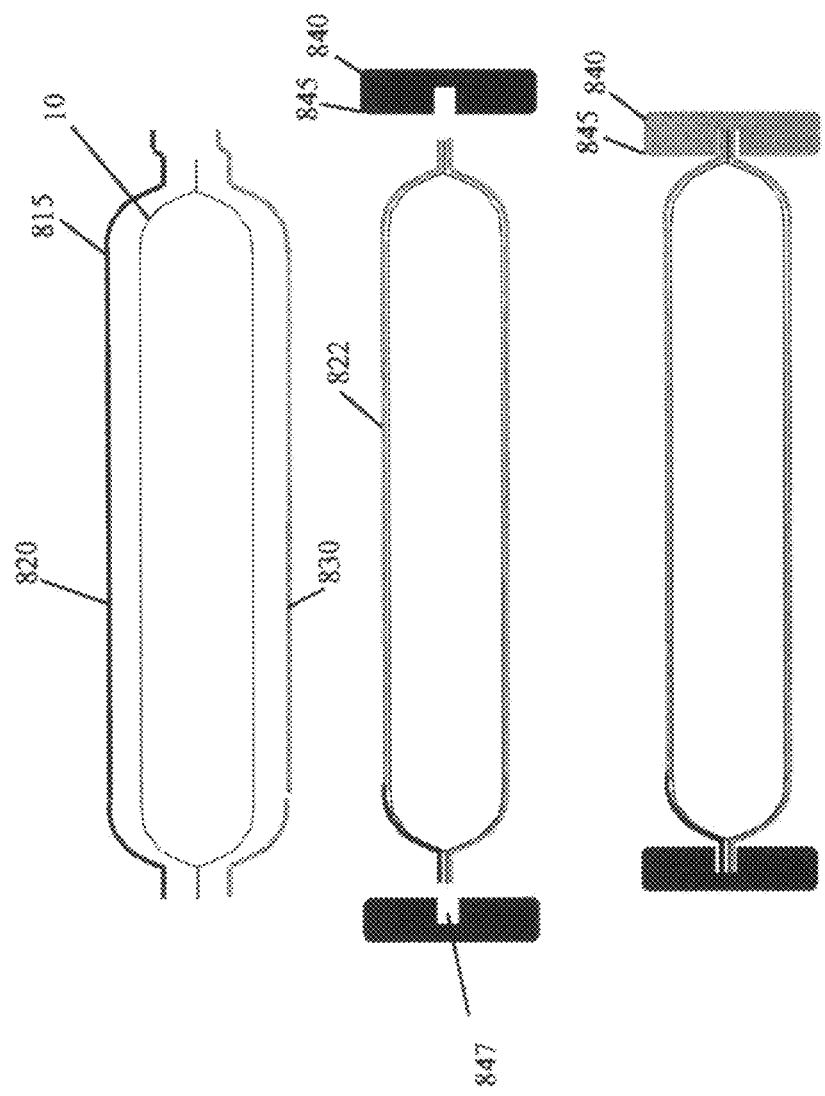

SYSTEMS AND METHODS FOR FREEZING, STORING AND THAWING BIOPHARMACEUTICAL MATERIALS

TECHNICAL FIELD

This invention relates, in general, to biopharmaceutical materials, preservation methods and systems, and more particularly to systems and methods for freezing, storing and thawing biopharmaceutical materials.

BACKGROUND ART

Preservation of biopharmaceutical materials, such as cryopreservation, is important in the manufacture, use, transport, storage and sale of such materials. For example, biopharmaceutical materials are often preserved by freezing between processing steps and during storage. Similarly, biopharmaceutical materials are often frozen and thawed as part of the development process to enhance the quality or to simplify the development process.

When freezing biopharmaceutical materials, the overall quality, and in particular pharmaceutical activity, of the biopharmaceutical materials is desirably preserved, without substantial degradation of the biopharmaceutical materials.

The preservation of biopharmaceutical material, particularly in bulk quantities, often involves placing a container containing liquid biopharmaceutical material in a cabinet freezer, chest freezer or walk-in freezer and allowing the biopharmaceutical material to freeze. Specifically, the container, which is typically one or more liters in volume and may range up to ten or more liters, is often placed on a shelf in the cabinet freezer, chest freezer or walk-in freezer and the biopharmaceutical material is allowed to freeze. These containers may be stainless-steel vessels, plastic bottles or carboys, or plastic bags. They are typically filled with a specified volume to allow for freezing and expansion and then transferred into the freezers at temperatures typically ranging from negative 20 degrees Celsius to negative 70 degrees Celsius or below.

Disposable bulk storage containers such as plastic bags or other flexible containers often are damaged, leading to loss of the biopharmaceutical material. Particularly, the volumetric expansion of the biopharmaceutical materials during freezing could generate excessive pressure in an over filled bag or in a pocket of occluded liquid adjoining the bag material, possibly leading to rupture or damage to the integrity of the bag. Moreover, handling of such disposable containers, such as plastic bags, during freezing, thawing, or transportation of these containers often result in damage thereof, due, for example, to shock, abrasion, impact, or other mishandling events arising from operator errors or inadequate protection of the bags in use.

Similarly, thawing of bulk biopharmaceutical materials may involve removing them from a freezer and allowing them to thaw at room temperature. In certain situations thawing can also lead to product loss. In addition, in certain situations rapid thawing of biopharmaceutical materials may result in less product loss than slower thawing. Further, it may also be desirable to control temperature of the biopharmaceutical materials during a thawing process since exposure of some biopharmaceutical materials to elevated temperatures in certain situations may also lead to product loss. For example, it may be desirable to maintain a thawing biopharmaceutical material at about 0° C. when still in liquid and solid form during thawing thereof. In situations where thawing is desirable it is necessary to protect the biopharmaceutical material from damage which may occur due to impact or rupture to the containers.

Thus, there is a need for systems and methods for freezing, thawing, and storing biopharmaceutical materials, including in bulk quantities, that do not result in loss of biopharmaceutical material, and are repeatable. In addition, there is a need for containers usable for the freezing, thawing and storing of biopharmaceutical materials, including in bulk quantities, which allow the freezing, thawing and transporting of biopharmaceutical materials therein without damage thereto, and which allow for the storage thereof to occur in an organized manner while protecting the biopharmaceutical material.

SUMMARY OF THE INVENTION

The present invention provides, in a first aspect, a system for use in freezing, storing and thawing biopharmaceutical materials which includes a holder and a container for holding biopharmaceutical materials therein. The holder has a cavity and the container is received in the cavity. The holder includes a first portion and second portion. The container is received between the first portion and the second portion to connect the container to the holder. The holder includes an interior cradle having a bottom and edges curving upwardly from the bottom. The cradle bounds the cavity. An outer rim is connected to the cradle and separated from the cavity. The bottom includes an inner surface facing the cavity receiving the container and an outer surface. The outer surface is recessed relative to an outer surface of the outer rim.

The present invention provides, in a second aspect, a system for use in freezing, storing and thawing biopharmaceutical materials which includes a container for holding biopharmaceutical materials therein. A holder has a cradle bounding a cavity and the container is received in the cavity. The holder includes a first portion and a second portion forming the cradle and the container is received between the first portion and the second portion to connect the container to the cradle. A support member protrudes from an outer surface of the cradle. The support member structurally supports the cradle and inhibits the deformation of the cradle in response to an expansion of biopharmaceutical material held in the container due to freezing.

The present invention provides, in a third aspect, a system for use in freezing, storing and thawing biopharmaceutical materials which includes a container for holding biopharmaceutical materials therein. A holder has a cradle bounding a cavity and the container is received in the cavity. The holder includes a first portion and a second portion forming the cradle and the container is received between the first portion and the second portion to connect the container to the holder. The holder includes an outer rim connected to the cradle. The outer rim includes a first plurality of outer teeth engageable with a second plurality of outer teeth of a second outer rim of a second holder to stack the holder and the second holder and to inhibit movement between the holder and the second holder.

The present invention provides, in a fourth aspect, a method for use in freezing, storing and thawing biopharmaceutical materials which includes providing a holder having a cavity and the holder having a first portion and a second portion. The holder has an interior cradle having a bottom and edges curving upwardly from the bottom. The cradle portion bounds the cavity. The holder has an outer rim connected to the cradle and separated from the cavity. The bottom includes an inner surface facing the cavity and an outer surface. The outer surface of the bottom is recessed relative to an outer surface of the outer rim. A container for holding biopharmaceutical materials is received in the cavity of the holder and between the first portion and the second portion to connect the container to the holder.

The present invention provides, in a fifth aspect, a method for use in freezing, storing and thawing biopharmaceutical materials which includes providing a holder having a first portion and a second portion forming a cradle bounding a cavity. A container for holding biopharmaceutical materials is received in the cavity of the holder and between the first portion and the second portion to connect the container to the holder. A support member protrudes from an outer surface of the cradle. The support member structurally supports the cradle and inhibits deformation of the cradle in response to an expansion of biopharmaceutical materials held in the container due to freezing.

The present invention provides, in a sixth aspect, a method for use in freezing, storing and thawing biopharmaceutical materials which includes connecting a container for holding biopharmaceutical materials to a holder by receiving the container in a cavity of a cradle of the holder. The cradle is formed by a first portion and a second portion of the holder. A first plurality of outer teeth of an outer rim of the holder is engaged with a second plurality of outer teeth of a second outer rim of a second holder to stack the holder and the second holder and to inhibit movement between the holder and the second holder.

BRIEF DESCRIPTION OF THE DRAWINGS

The subject matter which is regarded as the invention is particularly pointed out and distinctly claimed in the claims at the conclusion of the specification. The foregoing and other features, and advantages of the invention will be readily understood from the following detailed description of preferred embodiments taken in conjunction with the accompanying drawings in which:

FIG. 13 is a side cross-sectional view in simplified form of a portion of another holder in accordance with the present invention, receiving the container of FIG. 3;

FIG. 14 is a side cross-sectional view of the holder of FIG. 13 in simplified form showing top and bottom portions thereof exploded relative to a protective member thereof; and FIG. 15 is a side cross-sectional view in simplified form of the top and bottom portions of FIG. 14 connected to the protected member thereof.

DETAILED DESCRIPTION

In accordance with the principles of the present invention, systems and methods for freezing, thawing and storing biopharmaceutical materials are provided.

In an exemplary embodiment depicted in FIGS. 1-6, a system 5 for cooling, freezing, preserving, processing and thawing biopharmaceutical materials is shown. The system may include a sterile container, such as a flexible container 10, configured to contain the biopharmaceutical materials and configured to be supported by a supporting and/or protective structure, such as a holder 15.

Figure 1:
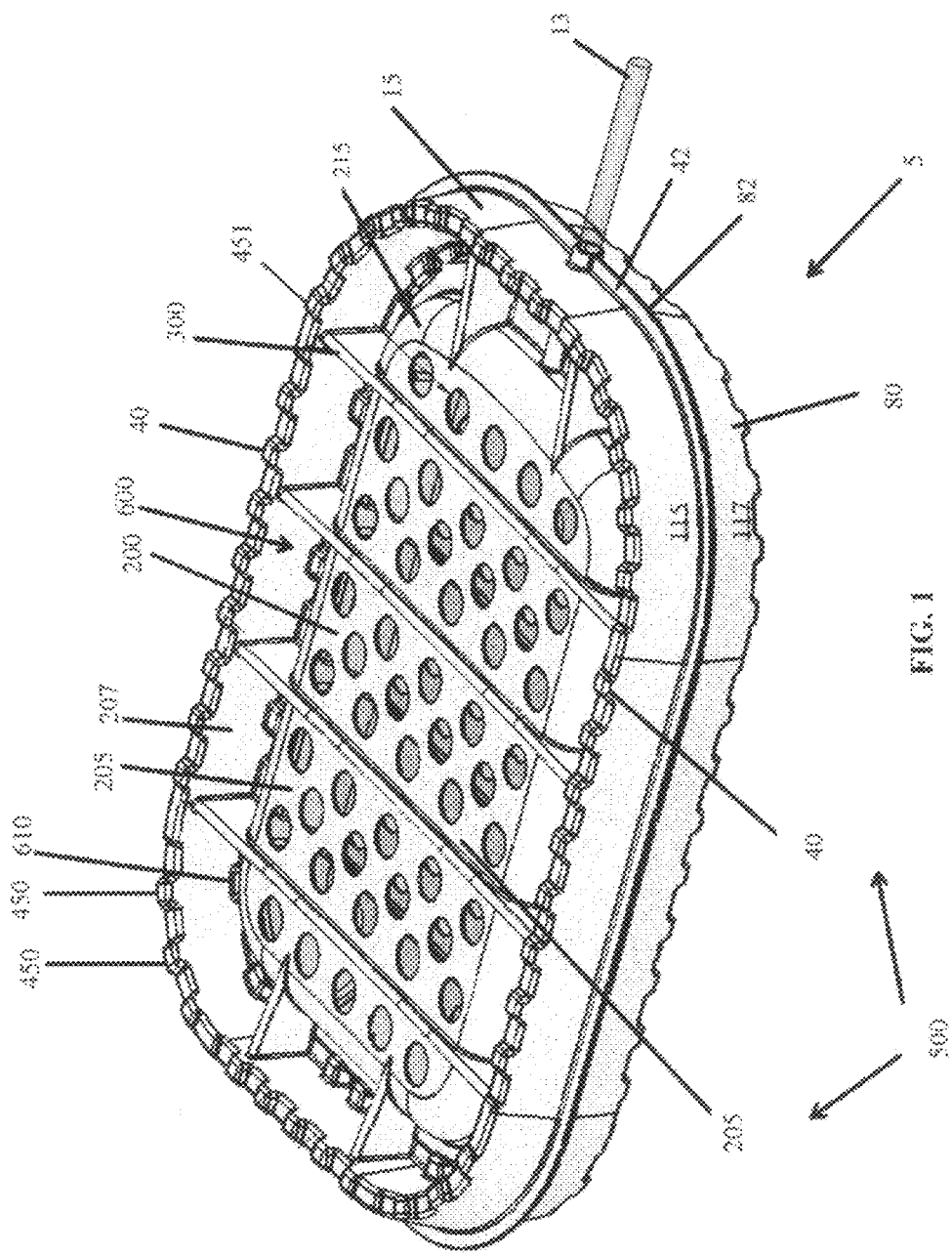
FIG. 1 is a perspective view of a holder receiving a container in accordance with the present invention.
Figure 3:
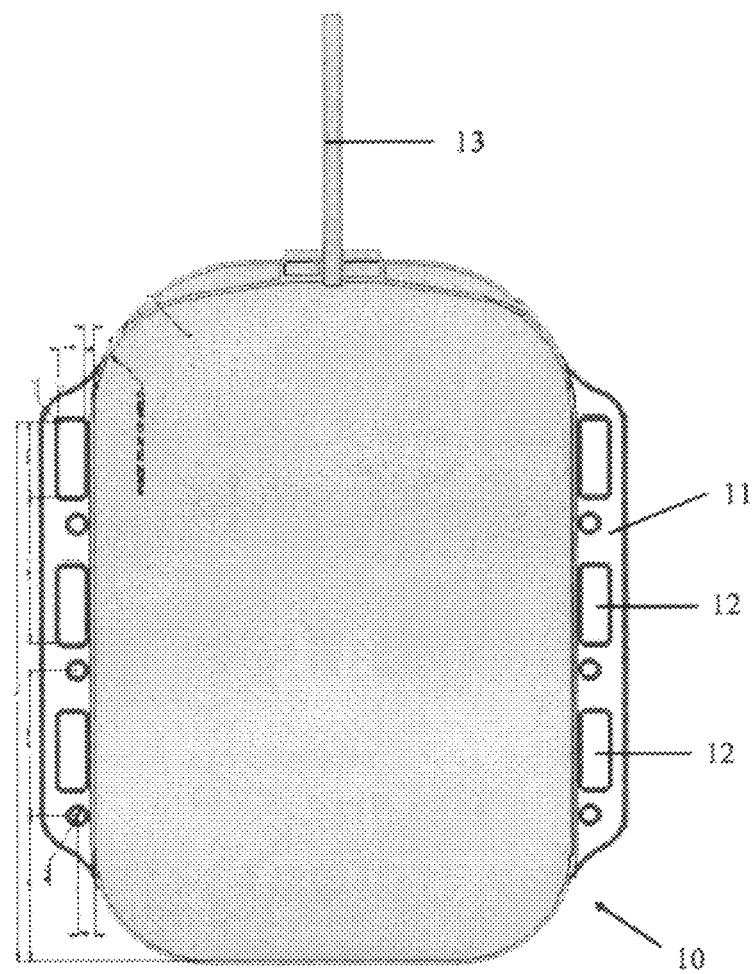
FIG. 3 is a top elevational view of a container receivable in the holder of FIG. 1.
Figure 4:
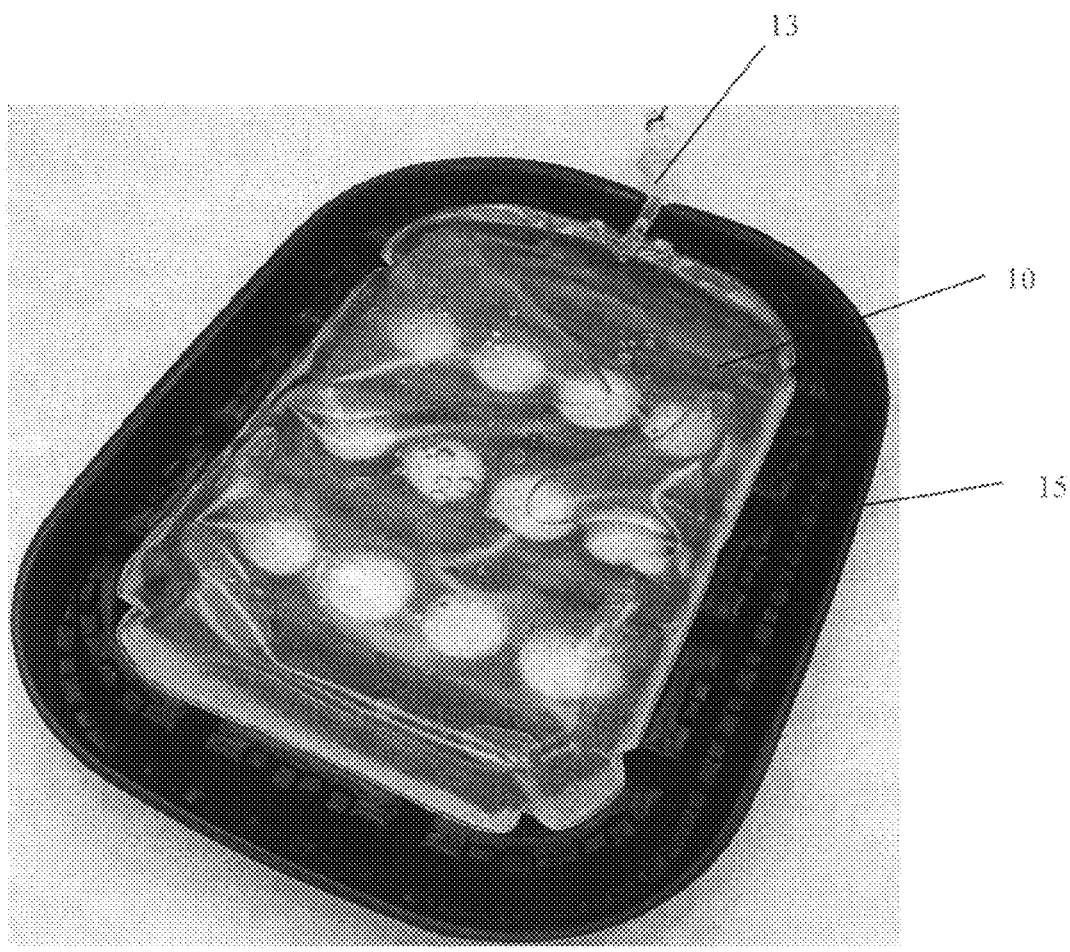
FIG. 4 is a perspective view of a portion of the holder of FIG. 1 receiving the container of FIG. 3.

Flexible container 10 may be formed of a laminated film which includes a plurality of layers and may have an interior volume ranging from 0.01-100 liters, (e.g., 0.1-20 L) as depicted in FIGS. 3-4 for example. Further, flexible container 10 could be available in a variety of sizes to accommodate different uses, for example, 5-10 liter flexible containers, such as 8-liter containers, may be utilized. Also a biocompatible product-contacting layer of the interior of flexible container 10 may be formed of a low density polyethylene, very low density polyethylene, ethylene vinyl acetate copolymer, polyester, polyamide, polyvinylchloride, polypropylene, polyfluoroethylene, polyvinylidenefluoride, polyurethane or fluoroethylenepropylene, for example. A gas and water vapor barrier layer may also be formed of an ethylene/vinyl alcohol copolymer mixture within a polyamide or an ethylene vinyl acetate copolymer. Further, flexible container 10 may include a layer with high mechanical strength (e.g. a polyamide), and an external layer with insulating effect to heat welding, for example, polyester. The layers may be compatible with warm and cold conditions and may be able to withstand ionizing and gamma irradiation for sterilization purposes. Also, flexible container 10 may have a large surface area to volume ratio, and a relatively thin wall thus promoting heat transfer therethrough when received in a temperature control unit such as an interior 500 of a walk-in or blast freezer (FIG. 1). One example of materials useful for formulation of flexible container 10 is described in U.S. Pat. No. 5,988,422 to Vallot, the entire subject matter of which is hereby incorporated herein by reference.

Container 10 may be adapted to receive and contain frozen and/or liquid biopharmaceutical materials. In an embodiment, the biopharmaceutical materials may comprise protein solutions, protein formulations, amino acid solutions, amino acid formulations, peptide solutions, peptide formulations, DNA solutions, DNA formulations, RNA solutions, RNA formulations, nucleic acid solutions, nucleic acid formulations, antibodies and their fragments, enzymes and their fragments, vaccines, viruses and their fragments, biological cell suspensions, biological cell fragment suspensions (including cell organelles, nuclei, inclusion bodies, membrane proteins, and/or membranes), tissue fragments suspensions, cell aggregates suspensions, biological tissues in solution, organs in solution, embryos in solution, cell growth media, serum, biologicals, blood products, preservation solutions, fermentation broths, and cell culture fluids with and without cells, mixtures of the above and biocatalysts and their fragments.

Container 10 may be configured (e.g., shaped and dimensioned) to be received in, and connected to holder 15 (FIGS. 1-2 and 4-5), which acts as a protector, supporting structure or frame for supporting flexible container 10. In one example, container 10 may have a pillow-shape. Holder 15 may be configured to protect a container held therein during filling, transport, storage, and/or freezing of biopharmaceutical materials. For example, holder 15 may hold and protect container 10 during freezing of biopharmaceutical materials in interior 500 of a walk-in or blast freezer (FIG. 1). Further, holder 15 may protect container 10 when holder 15 is stacked on or under another holder (e.g., holder 515, (FIG. 5)) similar to holder 15.

For example, holder 15 may include a first portion 115 and a second portion 117 forming a cradle 202 having a cavity 240 when connected to one another. First portion 115 has a bottom 200 and upwardly curving sides 210. Second portion 117 has a bottom 220 and upwardly curving sides 230. Bottom 200, upwardly curving sides 210, bottom 220 and upwardly curving sides 230 form cradle 202 which bounds cavity 240. Container 10 may be received in cavity 240 and may be connected to first portion 115 and/or second portion 117. For example, container 10 may be heat sealed or otherwise connected to first portion 115 and/or second portion 117 to prevent or inhibit separation of container 10 therefrom.

Figure 2:
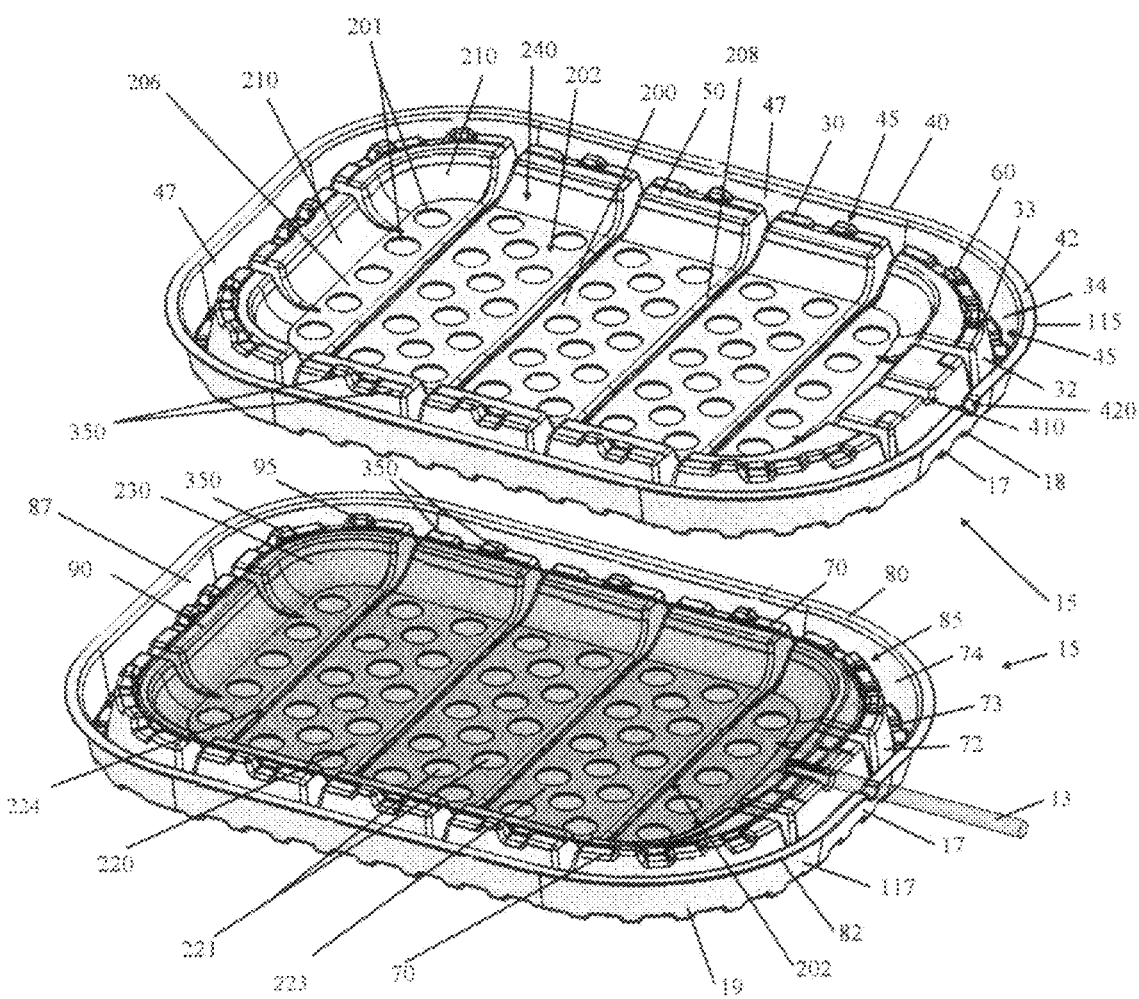
FIG. 2 is a perspective view of a first portion and second portion of the holder of FIG. 1.

An inner rim 30 of first portion 115 may be connected to an outer rim 40 of first portion 115 as depicted in FIG. 2. Inner rim 30 may include a substantially flat holding or clamping portion 50 and a connecting portion 60, both of which may extend partially or entirely around an inner circumference of holder 15. Similarly, an inner rim 70 of second portion 117 may be connected to an outer rim 80. Inner rim 70 may include a substantially flat holding or clamping portion 90 and a connecting portion 95, both of which may extend partially or entirely around an inner circumference of holder 15. Holding or clamping portion 50 and holding or clamping portion 90 may be configured to hold or clamp container 10 therebetween before it is filled with biopharmaceutical materials to center the container in the cradle and cavity 240. For example, holding portion 50 and holding portion 90 may be spaced from each other to provide a particular amount of friction to container 10 such that as container 10 is filled with the biopharmaceutical materials, an edge or portion of the container may move from a position between the holding portions, or external to the holding portions into cavity 240. Thus, as container 10 is filled with biopharmaceutical materials, container 10 may expand in cradle 202 to conform to the inner surfaces (i.e., bottom 200, upwardly curving sides 210, bottom 220 and upwardly curving sides 230) of cradle 202 bounding cavity 240. Also, container 10 may include an external flange 11 on opposite edges thereof configured to be received between holding or clamping portion 50 and holding or clamping portion 90 to hold the container in the cradle thereof. Such flange may be attached, or may be monolithic relative to, an outer circumference of the container and may be formed of the same material thereof.

Figure 6:
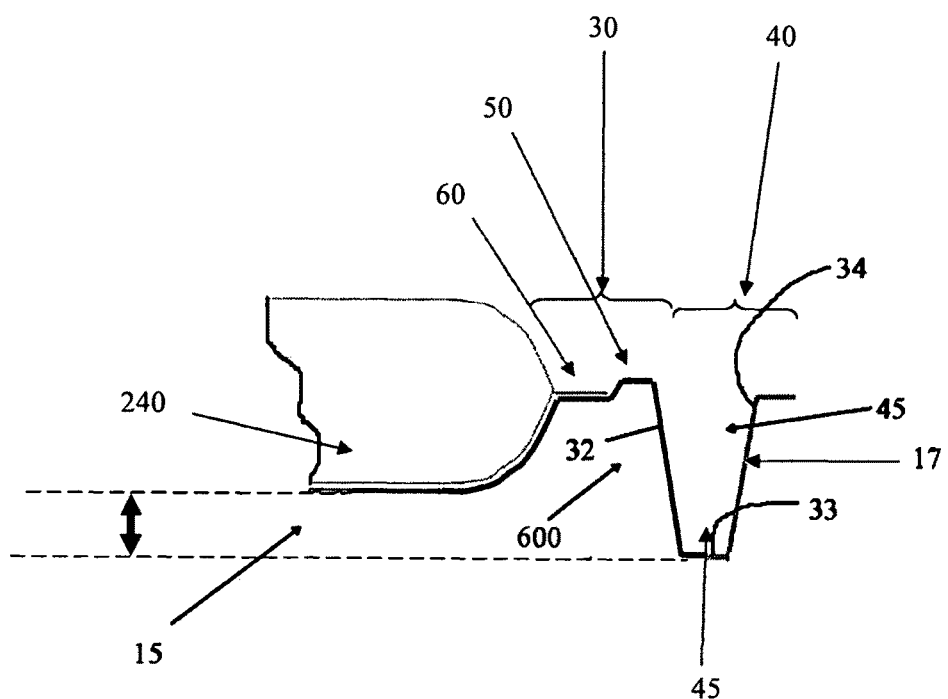
FIG. 6 is a side cross-sectional view of a portion of FIG. 2 showing a portion of a bottom portion of the holder receiving the container of FIG. 3 in simplified form.

A protective cavity 45 of holder 15 may be bounded by outer rim 40 which is connected to inner rim 30 as depicted in FIGS. 2 and 6. Also, a protective cavity 85 of second portion 117 may be bounded by outer rim 80 which is connected to inner rim 70. Protective cavity 45 and protective cavity 85 may extend circumferentially around holder 15. Outer rim 40 may include an inner wall 32 adjacent inner rim 30, a bottom surface 33 (corresponding to an opposite side of teeth 450) and an outer wall 34. Outer rim 80 may include an inner wall 72 adjacent inner rim 70, a bottom surface 73 and an outer wall 74. The protective cavities (i.e., cavity 45 and cavity 85) allow holder 15 to receive stresses, impacts, or shocks to an outer wall 17 of holder 15 while inhibiting or preventing damage to container 10 held in cavity 240. For example, an impact to outer wall 17 may cause outer wall 17 to temporarily move towards the inner rims into the protective cavities such that the outer walls of the outer rims absorb or dampen the shock and damage to the container is inhibited. Outer wall 17 may include outer wall 34 forming an exterior surface of outer rim 40 of first portion 115 and outer wall 74 forming an exterior surface of outer rim 80 of second portion 117. Outer wall 17 may be formed of an elastically deformable or resilient materials such as PET or HDPE. Further, each of first portion 115 and second portion 117 may be formed monolithically or they may be formed of separate elements connected together. Also, protective cavities 45 and 85 may provides storage for conduits including tubing, connectors and clamps therefor.

First portion 115 and second portion 117 may be connected together via engagement of connecting portion 95 and connecting portion 60. For example, each of connecting portion 60 and connecting portion 95 may include multiple teeth 350 extending upwardly away from bottom 200 and bottom 220, respectively. The teeth on connecting portion 95 and connecting portion 60 may alternate such that they may be inserted into the spaces between opposing teeth to connect (e.g., via interlocking the teeth) first portion 115 to second portion 117. The teeth may alternate continuously around perimeters of connecting portion 95 and connecting portion 60 or clusters of the teeth (e.g., teeth 350) may be intermittent around the perimeters thereof. The interlocking of the teeth of connecting portion 95 and connecting portion 60 may also support a sheer load during an impact or drop to avoid a sheer load being applied to the fasteners or welds connecting first portion 115 and second portion 117 to one another. Container 10 may include openings 12 (e.g., at or near outer edges thereof) to allow teeth to pass therethrough to connect container 10 to holder 15 and to inhibit movement of container 10 relative to holder 15 when the teeth are engaged and clamping portion 50 and connecting surface 90 abut container 10. In one example, the spacing of the teeth or groups of teeth intermittently may allow the connecting portions and/or holding portions (e.g., holding portion 50 and holding portion 90) to hold (e.g., inhibit movement of) the container in the portions of the inner rims between the teeth. In another example, a flange (e.g., flange 11) may be received between connecting portion 95 and connecting portion 60 without teeth 350 thereof passing through the openings (e.g., openings 12) in the container (e.g., container 10).

Bottom 200 and bottom 220 may include a plurality of first openings 201 and a plurality of second openings 221, which may allow heat transfer from an exterior of holder 15 to biopharmaceutical materials held in container 10 in cavity 240 of holder 15. Any number of apertures and any design or placement of the apertures relative to one another on the bottoms may be provided to facilitate such heat transfer while still allowing the bottoms to provide structure/support to a container in cradle 202. Further, the openings may be placed relative to one another and the container may be formed of material such that the container remains offset from the openings (i.e., toward an interior of the cradle) when the biopharmaceutical materials held therein are in a liquid form. The offset of the container's surface from the openings inhibits any potential damage to the container from external hazards which may come near bottom 200 or bottom 220.

Also, bottom 200, bottom 220, sides 210 and sides 230 of cradle 202 may be connected to outer rim 40 by one or more support members or support ribs 300 providing structural support as depicted in FIG. 1, for example. Such ribs may extend across bottom 200 to connect bottom 200 and opposite sides of outer rim 40 to one another. Also, the ribs may extend across bottom 220 to connect opposite sides of outer rim 80 to one another and to bottom 220. Alternatively, one or more of ribs 300 may extend from outer rim 40 to bottom 200 or sides 210 without extending from one side of outer rim 40 to another side thereof. Ribs 300 may be raised relative to an exterior surface 205 of bottom 200 as depicted in FIG. 1. An interior side 206 of bottom 200 may also include grooves 208 (FIG. 2) which correspond to ribs 300 on exterior surface 205 of bottom 200. Similarly, ribs 300 may be connected to bottom 220 and sides 230 and/or to opposite sides of outer rim 80 to provide structural support to cradle 202. Also, ribs 300 may be raised relative to an exterior surface (not shown) of bottom 220 while an interior surface 223 may have grooves 224. The connection of support ribs (e.g., ribs 300) to cradle 202 structurally supports the cradle and inhibits deformation of a shape of the cradle in response to expansion of biopharmaceutical materials held in container 10 due to freezing. In another example, holder 15 may not have ribs 300 and instead may be reinforced by rods or cushioned by pads formed of textiles, foam, or other resilient materials.

As indicated above, the container (e.g., container 10) may avoid extending into openings 201 and 221 when biopharmaceutical materials held in the container are in a liquid form. Further, the container may also avoid extending into grooves 208 when such biopharmaceutical materials are in a liquid form. Upon the biopharmaceutical materials undergoing a freezing process, the container and biopharmaceutical materials held therein may extend into grooves 208, openings 201, and openings 221. The movement of freezing biopharmaceutical materials into grooves 208, openings 201, and openings 221 provide locations for expansion of the biopharmaceutical materials thereby allowing for less expansion of bottom 200 and bottom 220 in directions away from one another than would otherwise be the case absent the movement of biopharmaceutical materials into these locations.

Further, a space 600 may extend between exterior surface 205 of bottom 200 and an exterior surface 207 of inner wall 32 of outer rim 40 as depicted in FIGS. 1 and 6. Space 600 may also be bounded by an exterior surface 215 of upwardly extending sides 210 and a bottom 610 of space 600, which may be an exterior surface corresponding clamping portion 50 and connecting surface 90 on the opposite of holder 15. As described above relative to protective cavity 45 and protective cavity 85, the space between outer rim 40 and exterior surface 205 of bottom 200 may provide protection to container 10 held in cradle 202. In particular, an impact, shock or stress to outer rim 40 may cause outer rim 40 (e.g., exterior surface 207) to move into, or deform (e.g., elastically or resiliently) toward space 600 thereby absorbing the impact, shock or stress and inhibiting the impact, shock or stress from being applied to container 10 and the biopharmaceutical materials held therein. Similarly, a space (not shown) may be provided between an exterior surface (not shown) of bottom 220 and outer rim 80 to inhibit damage to container 10 and biopharmaceutical materials held therein.

Outer rim 40 may have a height different than exterior surface 205 of bottom 200 and ribs 300 thereon such that outer rim 40 is raised relative to exterior surface 205 and ribs 300 as depicted in FIG. 1. The difference in height between the outer rim and the exterior surface of the bottom of the holder allows expansion of biopharmaceutical materials held in container 10 in cradle 202 due to freezing while avoiding the exterior side (i.e., exterior surface 205) extending beyond outer rim 40. Similarly, outer rim 80 may have a height different than the exterior surface (not shown) of bottom 220 and ribs 300 thereon such that outer rim 80 is raised relative to the exterior surface and ribs 300 thereby allowing expansion of biopharmaceutical materials held in container 10 in cradle 202 due to freezing while avoiding the exterior side of bottom 220 from extending beyond outer rim 80.

Figure 7:
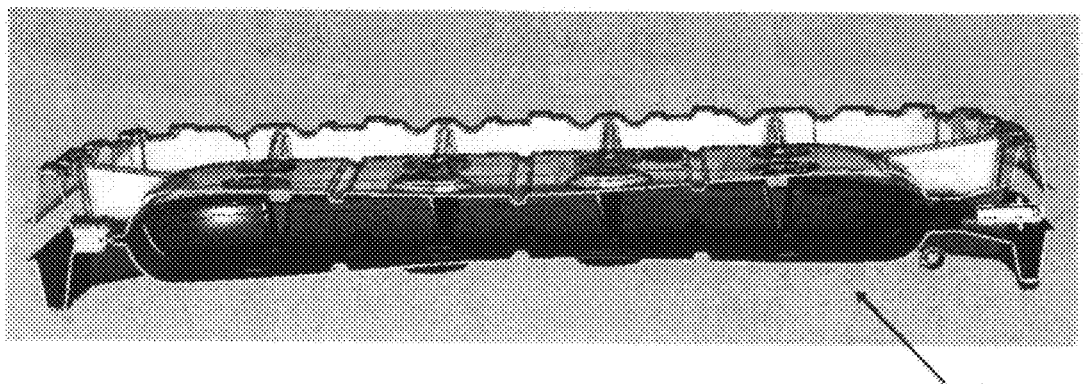
FIG. 7 is a cross-sectional view of another holder in accordance with the present invention and showing opposite bottom portions curving toward each other.

Further, water and aqueous solutions expand by about ten percent when frozen and such expansion may be non-uniform. In one example, when container 10 is received in cradle 202 the container may be filled with biopharmaceuticals such that cradle 202 may accommodate the expansion due to freezing of the biopharmaceutical materials, i.e., the cradle is not filled with biopharmaceutical materials to its volumetric capacity in a liquid state and instead space exists to allow expansion of the biopharmaceutical materials within cradle 202. Also, in another example bottoms 200 and 220 of cradle 202 may curve inwardly toward one another (i.e., the shape thereof may be concave when viewed from an exterior of cradle 212 as depicted in FIG. 7) before freezing of biopharmaceutical materials and the expansion of the biopharmaceutical materials may cause the bottoms to move apart from each other such that they are substantially flat on outer surfaces (e.g., exterior surface 205) thereof.

Figure 5:
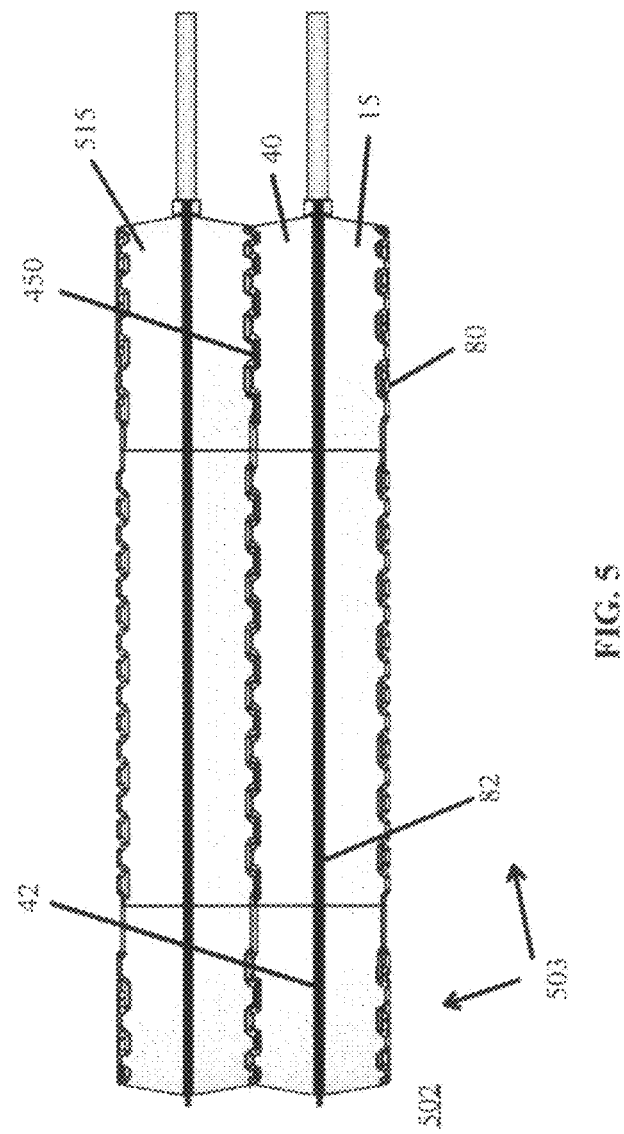
FIG. 5 is a side elevational view of the holder of FIG. 1 stacked on a second holder in accordance with the present invention.

Further, the difference in height between each of the outer rims and the exterior surfaces of the bottoms of the holder (i.e., even after freezing of the biopharmaceutical materials) inhibits damage to the biopharmaceutical materials held in container 10, along with container 10 itself. In particular, the bottoms (e.g., bottoms 200 and 220) of the holder may not contact any objects adjacent to holder 15 or abutting holder 15 resulting from such objects instead contacting the outer rim (s), as depicted in FIG. 5. For example, when holder 15 lies horizontally on a surface 502 of an interior (e.g., an interior 502) of a blast freezer, outer rim 80 may contact the surface and outer rim 40 may contact an object (e.g., a holder 515) stacked on top of holder 15, but neither bottom 200 nor bottom 220 may contact the surface or the object due to the space between the exterior surface (e.g., exterior surface 205) of the bottoms and any object resulting from the difference in height between the outer rims and the exterior surfaces of the bottoms.

The outer rims (e.g., outer rim 40 and outer rim 80) may also have teeth 450 (FIG. 1) to allow holder 15 to be connected (i.e., by interlocking the teeth) to a second similar holder, such as holder 515, having complementary teeth on an outer rim thereof as depicted in FIG. 5. The difference in height between the outer rims and exterior surfaces also allows the stacking of multiple holders (e.g., holder 15 and holder 515) on the outer rims thereof and the engagement of the corresponding teeth in contrast to stacking the exterior surfaces (e.g., exterior surface 205) on each other. For example, the difference in heights between the outer rims and exterior surfaces is advantageous particularly when such exterior surfaces (e.g., exterior surface 205) may be deformed (e.g., by a mounding effect) due to the expansion of freezing biopharmaceutical materials held in containers therein thereby making stacking difficult. In this case, the stacking of the holders on the outer rims minimizes any interference that may be caused by deformation of the exterior surfaces. More particularly, the height difference between the rims and the exterior surfaces allow the expansion of the biopharmaceutical materials held in container 10 in cradle 202 toward an outer surface of the outer rim (e.g., outer rims 40 and 80) while avoiding the exterior surfaces from extending beyond the outer surfaces of the outer rims. The expansion of the exterior surface beyond the outer rims may otherwise (i.e., absent the raised height of the rims relative to the exterior surfaces) inhibit the stacking of another holder on top of holder 15 due to the uneven surfaces provided by the expansion of the biopharmaceuticals held in container 10.

Outer rim 40 may include a bottom end 42 and outer rim 80 may include a top end 82, which may be connected to one another via heat sealing, or some other means of fixedly and/or sealingly connecting the outer rims to one another as depicted in FIGS. 1, 2 and 4. For example, flanges (not shown) may also be provided which extend outwardly from outer rims 40 and 80 to allow first portion 115 and second portion 117 to be mechanically fastened to each other using fasteners, such as pop rivets, ratcheting fasteners, other fasteners, screws or bolts. Also, such connection may be done by welding (e.g., heat sealing, high frequency sealing or ultrasonic welding) or with adhesive. Such a connection may inhibit contamination from passing by outer rim 40 and outer rim 80 toward container 10.

The outer rims (e.g., outer rim 40 and outer rim 80) and the inner rims (e.g., inner rim 30 and inner rim 70) may include apertures such as a first aperture 420 and a second aperture 410 depicted in FIG. 2 to allow conduits (e.g., a conduit 13) connected to container 10 to pass therethrough. Such conduits may allow filling or draining of biopharmaceutical materials or other solids, liquids, or gases into and/or out of the interior (not shown) of container 10. Conduit 13 may also be used to insert a measurement probe (not shown) inside container 10 (e.g., a pH electrode, a conductivity sensor, temperature probe, an ion selective electrode, a spectophotometric probe, an ultrasound sensor, an optic fiber.)

Conduit 13 may be integral (e.g., monolithic relative) to container 10 or it may be connectable to a receiving port (not shown) thereof. For example, conduit 13 could be connected to a receiving port using a fitting placed within the inlet port. Fittings such as those described in U.S. Pat. No. 6,186,932, may be used for the connection of such conduits. Also, fittings which can maintain the sterility of the contents of the container or flexible container may preferably be used. The fittings may be configured in different shapes, such as straight fittings and/or angled fittings including ninety (90) degree elbows, if desired. In another example, conduit 13 may include a filter (not shown) to filter any impurities or other undesirable materials from the biopharmaceutical material. The conduit and/or fittings may be located in protective cavity 45 and/or protective cavity 85, which may protect conduit 13 and the fittings from any damage resulting from impact or stress, such as the impact resulting from a person dropping holder 15 when container 10 is filled with biopharmaceutical materials.

Figure 8:
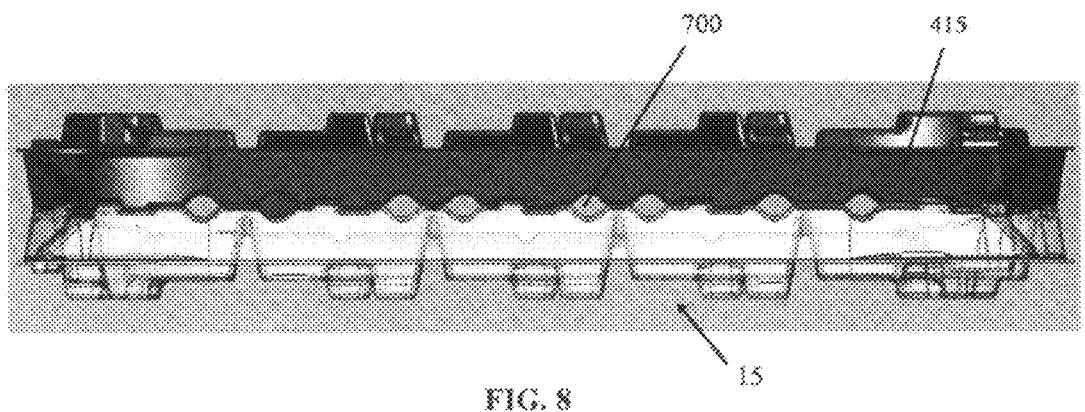
FIG. 8 is a side-elevational view of another holder in accordance with the present invention showing the first portion of a first holder stacked on the second portion of a second holder

In another example depicted in FIG. 8, the outer rims (e.g., outer rim 40 and outer rim 80) may also have spaces 700 (FIG. 8) that form channels when holder 15 is connected (i.e., by interlocking teeth 450) to a second similar holder, such as a holder 415, having complementary teeth and spaces on an outer rim thereof as depicted in FIG. 8. Spaces 700 may allow heat transfer from an exterior of holder 15 to the exterior surface of a bottom 200 and a bottom 220 of the holder 15 and to the biopharmaceutical materials held in container 10 in cavity 240 of holder 15. Any number of spaces or channels and any design or placement of the spaces or channels relative to one another may be provided to facilitate such heat transfer. Hanging holes (not shown) may be located on inner rim 30 or outer rim 40 of first portion 115 and on matching locations on inner rim 70 or on outer rim 80 of second portion 117. Such hanging holes allow a hanger (not shown) to be inserted therein to allow holder 15 to be suspended from such hanger. Biopharmaceutical materials held in container 10 may then be drained through a conduit, such as conduit 13.

Figure 9:
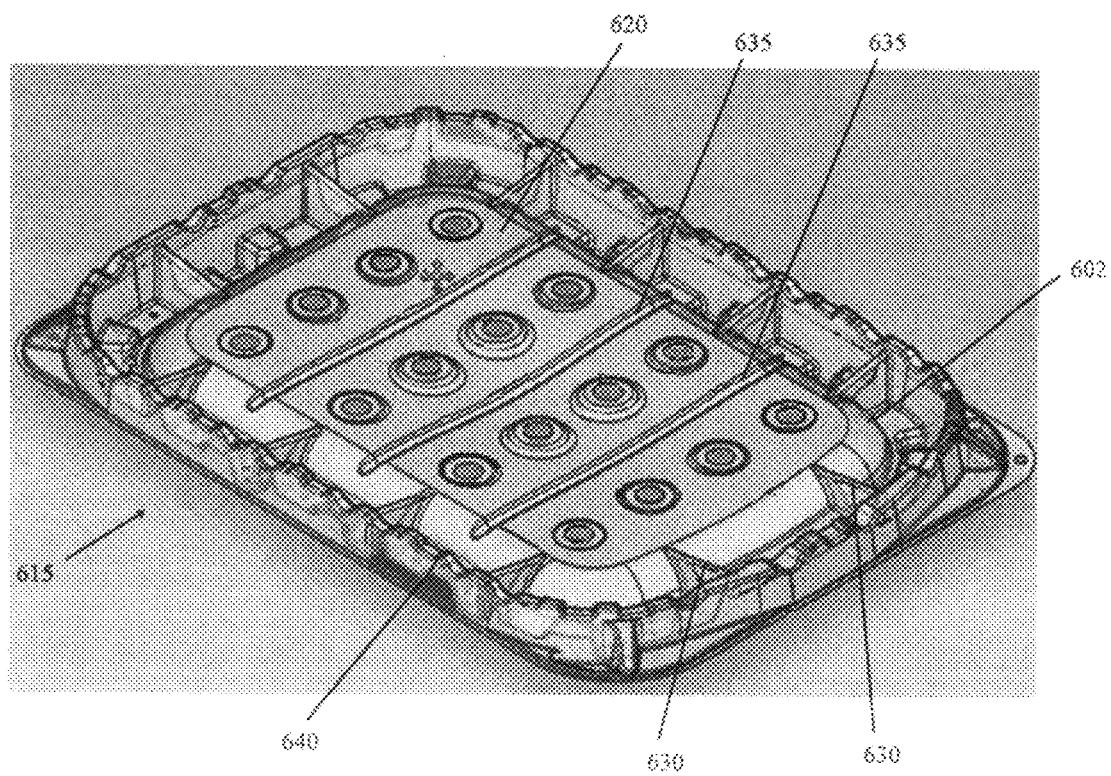
FIG. 9 is a perspective view of a top portion of another holder in accordance with the present invention.
Figure 10:
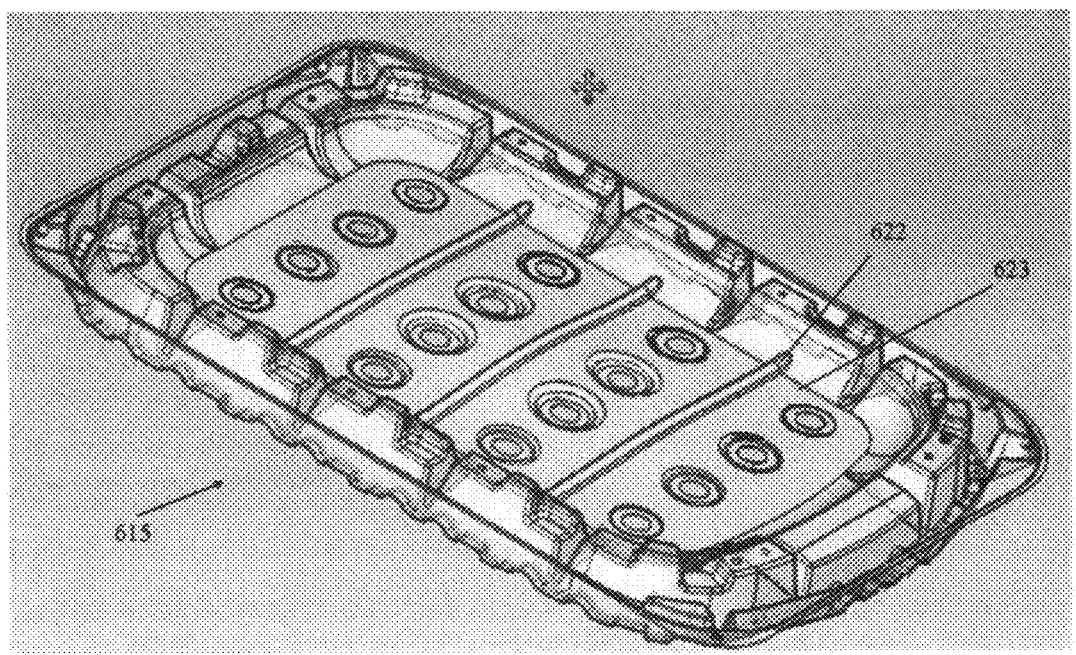
FIG. 10 is a perspective view of a bottom portion of the holder of FIG. 9.
Figure 11:
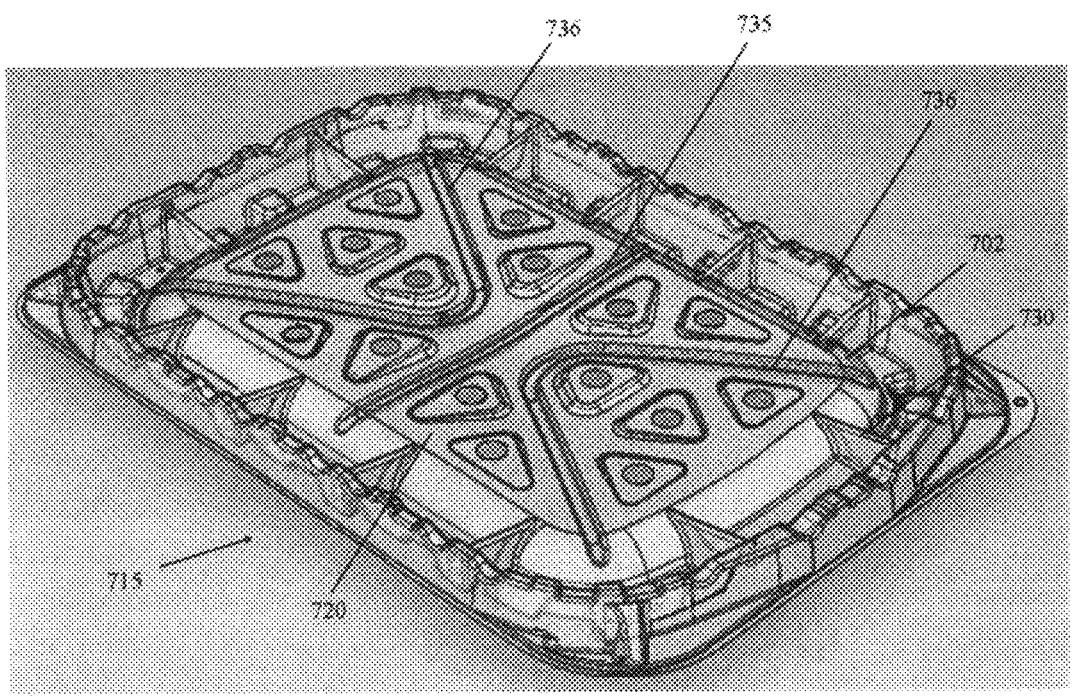
FIG. 11 is a perspective view of a top portion of a further holder in accordance with the present invention.
Figure 12:
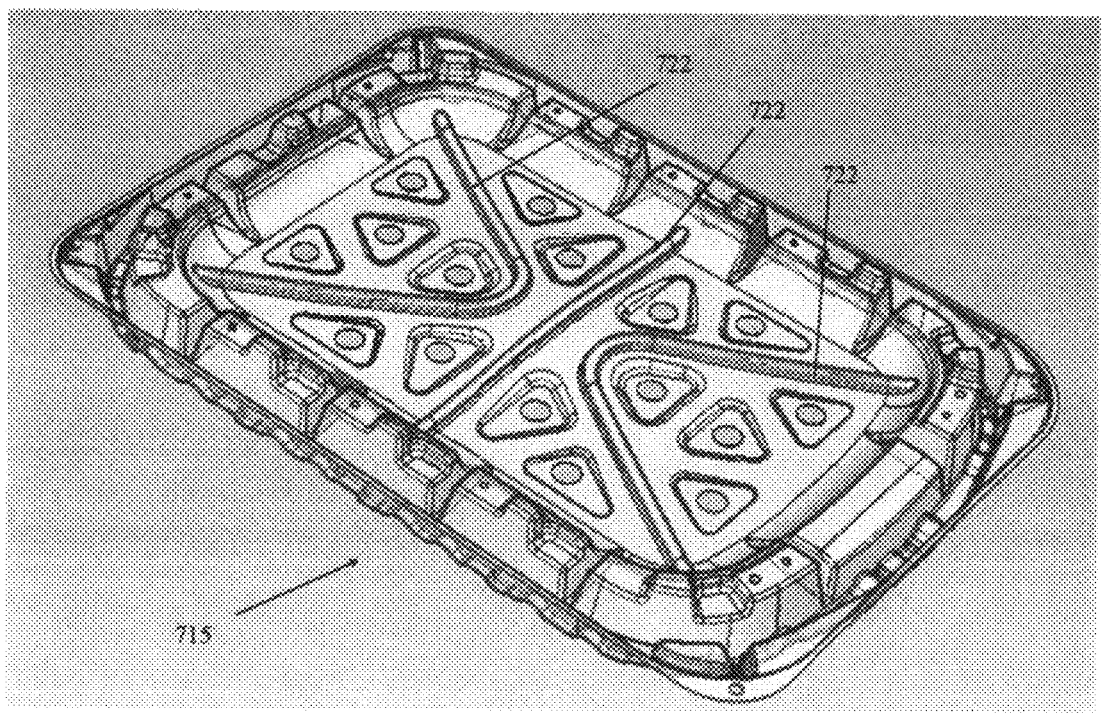
FIG. 12 is a perspective view of a bottom portion of the holder of FIG. 11.

In another example depicted in FIGS. 9-10, a holder 615 includes a plurality of connecting ribs 630 and a plurality of transverse ribs 635. Connecting ribs 630 connect an outer rim 640 to a cradle 602, which is similar to that described for holder 15. Further, transverse rib 635 extend transversely relative to a longitudinal dimension of a bottom 620 of cradle 602 and from one side of the cradle to an opposite side thereof. Grooves 622 are located on an opposite surface 623 of bottom 620 and the grooves correspond to transverse ribs 635. The bottom may be concave inwardly as viewed from outside cradle 602, as described above for holder 15 depicted in FIG. 7. Ribs 630 and transverse ribs 635 provide support for cradle 602 to inhibit deformation of bottom 620 away from cradle 602 in response to the freezing of biopharmaceutical materials held in cradle 602. In a further example depicted in FIGS. 11-12, a holder 715 includes connecting ribs 730, a transverse rib 735, and opposite curving ribs 736 which extend from opposite ends of a cradle 602 toward transverse rib 735 and curve back toward the end from which they started. As it is understood by one skilled in the art, support ribs may extend in various directions on a cradle, such as cradle 602 or cradle 702, to provide structural support to a cradle in response to biopharmaceutical materials freezing which are held in such a cradle. As depicted in FIG. 12, grooves 722 correspond to the ribs on an opposite side of a bottom 720 such that the grooves are indentations and the ribs are protrusions from opposite sides of bottom 720.

In another example depicted in FIGS. 13-15, a holder 815 may receive container 10 and may include a first portion 820 and a second portion 830 which may be connectable to a protective member 840 which may completely or partially surround first portion 820 and second portion 830. Protective member 840 may be formed of a resilient material (e.g., PET or HDPE) configured to absorb stresses or shocks thereon. Protective member 840 may be connected to first portion 820 and second portion 830 via a friction fit, for example. Alternatively, ends 825 of first portion 820 and second portion 830 may be received in a groove 847 of multiple portions of member 840. Such multiple portions of protective member 840 may then be welded or otherwise connected to one another. As depicted, an exterior surface 822 of first portion 820 may be recessed relative to a top surface 845 of member 840. The recessed location of exterior surface 822 may inhibit damage to container 10 held therein as described above relative to holder 15.

Also, the holders (e.g., holder 15) may preferably be formed of materials configured to support a weight of container 10 and to protect container 10 from being punctured or damaged due to an impact or stress on holder 15. For example, holder 15 may be more rigid than container 10 held therein. Also, the materials forming holder 15 may remain stable and retain their structural properties over a large range of temperatures. Specifically, such materials should retain their load-bearing capacity and exhibit cold crack temperatures no higher than negative 80 degrees Celsius while being resistant to cleaning agents and methods commonly used in biopharmaceutical manufacturing, e.g., sodium hydroxide, sodium hypochloride (e.g., CLOROX), peracetic acid, etc. For example, first portion 115 and second portion 117 of holder 15 could be formed of injection molded plastic or thermo formed plastic, such as PET (e.g., Clear 0.05" PET) or HDPE (e.g., 0.080" black unfilled HDPE). Also, holder 15 may be formed of fluoropolymer resin (e.g. TEFLON), machined plastic, stainless steel or any number of other materials including aluminum, polyethylene, polypropylene, polycarbonate, and polysulfone, for example. Further materials may include composite materials such as glass-reinforced plastic, carbon-fiber reinforced resins, or other engineering plastic materials known to offer high strength-to-weight rations and which are serviceable at various temperatures of interest. It will be understood by those skilled in the art that each of first portion 115 and second portion 117 may be monolithic and formed as one piece or may include elements fixedly connected together. In addition, portions 115 and 117 may be constructed as one piece such that the portions 115, 117 may be hinged or otherwise connected together. Further, holder 15 could be formed of a single material (e.g., injection molded plastic) or it could be formed of different materials and connected together. Also, holder 15 may be formed of a material compatible with gamma radiation.

Also, a holder (e.g., holder 15) may be formed, sized and/or dimensioned to receive and support containers of various sizes to provide additional rigidity and support to the container(s), thus facilitating handling, storage, and/or temperature control thereof. For example, container 10 may be pillow shaped and holder 15 may be elliptically shaped.

Also, it will be understood by one skilled in the art that various holders (e.g., holder 15) may have cradles (e.g., cradle 202) configured (e.g., shaped and dimensioned) to receive various sized containers (e.g., container 10) and to be received in a temperature control unit (e.g., a blast freezer). Although the containers are described herein as flexible containers, the containers may be made of a semi-rigid material such as polyethylene or the like. An example of such a container could include a container similar to a standard plastic milk jug. Containers made of such similar semi-rigid materials may benefit from additional rigidity supplied by attachment (e.g., fixedly or releasably) to a holder, for example. Further, the containers whether formed of a rigid, flexible or semi-rigid material, contain outer surfaces which may contact the interior surfaces of a holder which may include holes and/or may be formed of a material to facilitate heat transfer to and from a container (e.g., container 10) held in such a holder (e.g., holder 15) when the holder is present in a temperature control unit, such as a blast freezer. Further, the outer surfaces of the holder receiving the containers for holding the biopharmaceutical materials may be in contact with air flow in an interior (e.g., interior 500) of a blast freezer or other means of temperature control to cause the cooling and/or heating of the container having the biopharmaceutical materials therein to cause the temperature of the biopharmaceutical materials to be controlled.

In another example, holder 15 may be formed of a foam (e.g., HDPE, EVA), or a more rigid material (e.g., foam or solid) may be utilized with such a foam to form the holder. Also, a container, such as container 10, may be connected to a holder, such as holder 15, by RF welding. In a further example, a container and holder may be separated from one another within cradle 202 by a layer of collapsible dimples (not shown) or ribs (not shown).

The biopharmaceutical material in the containers (i.e., container 10) and holders (e.g., holder 15) described above may thus be cooled or otherwise thermoregulated (e.g., to a sub-zero temperature) in a temperature control unit, such as a blast freezer providing forced convection, for example. Alternatively, the biopharmaceutical materials may be frozen in a conventional laboratory freezer providing free convention, a plate freezer or via a liquid nitrogen path. When such freezing operation is completed, the containers may be removed from the temperature control unit by removing the containers and the holders, or other support structures which the containers are received in or connected to, for example. The holders or other support structures holding the containers may be stored in a large chiller or freezer with an interior air temperature of about negative 20 degrees Celsius, for example.

A typical process for processing and/or preserving a biopharmaceutical material is described as follows. One or more containers (e.g., container 10) is received in and/or connected to a holder (e.g., holders 15, 515) as depicted in FIG. 4. Also, holder 15 may be aligned substantially horizontally (e.g., as depicted in FIGS. 1 and 5) and biopharmaceutical material, for example liquid biopharmaceutical material, may be inserted through conduit 13 into container 10. Also, after biopharmaceutical material is received in the interior of the holder (e.g., holders 15, 515) through a conduit (e.g., conduit 13). Holder 15 may be located in a temperature control unit, such as an interior 500 of a blast freezer, as shown in FIG. 1. The biopharmaceutical contents are frozen in the temperature control to negative 20 degrees Celsius or below, for example. After the biopharmaceutical material in the container(s) is frozen, holder 15 and the container(s) may be stored in the temperature control unit, such as a blast freezer, or removed therefrom and placed in a large freezer, for example, a walk-in freezer having an interior air temperature of about negative 20 degrees Celsius for storage, as is typically present in large medical institutions (e.g., hospitals). Also, the use of containers (e.g., container 10) having a uniform thickness allow uniform cooling to occur within such a temperature control unit, blast freezer, or other means for controlling a temperature of the immediate surroundings of such containers.

Further, the above-described containers may be removed from a freezer or other system for storage of the flexible containers and contents thereof at a controlled temperature. These containers having biopharmaceutical material therein may then be received in a temperature control unit (e.g., an interior 500 of a blast freezer) for heating, melting, agitating, mixing and/or thawing the biopharmaceutical material contained in the containers. For example, holder 15 supporting container 10 having frozen biopharmaceutical material therein may be placed in a temperature control unit where its temperature may be controlled (e.g. thawed) by heat transfer plates or air convection (e.g., free or forced air) heating. Also, the biopharmaceutical materials may be thawed in a water bath or in air and ambient temperature. In another example, a thin film heater, such as self-regulating positive temperature coefficient (PTC) heater element, may be incorporated into holder 15 to allow a container held therein to be thawed at a predefined setpoint using only an external voltage source. In addition, holder 15 may be submitted to gentle mixing inside a temperature control unit to accelerate the thawing kinetics and to minimize any solute concentration gradient in the thawed liquid.

From the above description, it will be understood to one skilled in the art that the containers described herein may be adapted for use in holders of various shapes or sizes. Further, the holders may be adapted to receive containers of various shapes or sizes. These holders or support structures may be configured for long or short term storage of the containers containing biopharmaceutical materials in liquid or frozen state, or may be adapted to transport the flexible containers containing biopharmaceutical materials in liquid or frozen state. Further, these holders and containers may be adapted for utilization with materials other than biopharmaceutical materials.

While the invention has been depicted and described in detail herein, it will be apparent to those skilled in the relevant art that various modifications, additions, substitutions and the like can be made without departing from the spirit of the invention and these are therefore considered to be within the scope of the invention as defined in the following claims.

The invention claimed is:

1. A system for use in freezing, storing and thawing biopharmaceutical materials, said system comprising:
   a container configured to contain biopharmaceutical materials therein;
   a holder having a cavity, said container received in said cavity;
   said holder comprising a first portion and a second portion forming an interior cradle, said container received between said first portion and said second portion to connect said container to said holder;
   said first portion having a first bottom and first edges extending from said first bottom and forming a first inner rim, said first bottom and said first edges bounding said cavity, said inner rim extending completely around a perimeter of said container, said first inner rim comprising longitudinal sides, ends, and curved corners surrounding said perimeter, each of said corners connecting a longitudinal side of said longitudinal sides to an end of said ends, said container contacting said first bottom, said first edges, and at least one corner of said corners;
   said first edges comprising curved surfaces having first edge axes about perpendicular to axes of said curved corners;
   said second portion comprising a second bottom bounding said cavity opposite said first bottom and second edges extending from said second bottom and bounding said cavity, said second edges comprising second curved surfaces having second edge axes about perpendicular to said axes of said curved corners, said container contacting said second bottom and said second edges;
   said first portion comprising an outer rim connected to said cradle and separated from said cavity and said inner rim; and
   wherein said first bottom comprises an inner surface facing said cavity receiving said container and an outer surface, said outer surface of said first bottom being recessed towards said container relative to an outermost surface of said outer rim such that said outermost surface is located further away from said second portion than said outer surface of said bottom is located away from said second portion.

2. The system of claim 1 wherein each of said first curved surfaces and each of said second curved surfaces opposite each other about said cavity having a common axis or a parallel axis relative to each other.

3. The system of claim 1 wherein said inner rim is configured to hold said container in said cradle and to allow said container to move from outside the cradle into the cradle in response to biopharmaceutical material being inserted into said container.

4. The system of claim 3 wherein said second portion comprises a second inner rim and said second inner rim comprises a second substantially flat holder portion configured to engage said inner rim to hold said container and to allow said container to move from outside said cradle into said cradle in response to biopharmaceutical material being inserted into said container.

5. The system of claim 1 further comprising a support rib protruding from an outer surface of said cradle, said rib structurally supporting said cradle to substantially maintain a shape of said cradle in response to an expansion of biopharmaceutical material held in said container due to freezing.

6. The system of claim 5 wherein said support rib extends from a side of said cradle to an opposite side of said cradle.

7. The system of claim 1 wherein said biopharmaceutical materials comprise liquid biopharmaceutical materials.

8. The system of claim 1 wherein said first portion comprises a first inner rim and said second portion comprises a second inner rim, said first inner rim comprising a first plurality of teeth and said second inner rim comprising a second plurality of teeth, said first plurality of teeth and said second plurality of teeth engageable with each other to connect said first inner rim to said second inner rim.

9. The system of claim 1 wherein said second portion comprises a second outer rim separated from said cavity.

10. The system of claim 9 further comprising at least one conduit extending from said container through at least a second cavity to an exterior of said holder, said at least one conduit providing communication between said container and the exterior of said holder.

11. The system of claim 9 wherein a protective cavity is bounded by said outer rim and said second outer rim.

12. The system of claim 1 wherein said outer rim comprises a first plurality of outer teeth engageable with a second plurality of outer teeth of a second outer rim of a second holder to inhibit movement between said holder and the second holder.

13. The system of claim 9 wherein said outer surface of said bottom is recessed toward said cradle relative to said outer surface of said outer rim by an amount dimensioned to allow for expansion of biopharmaceutical materials such that said outer surface avoids extending beyond said outer rim.

14. A system for use in freezing, storing and thawing biopharmaceutical materials, said system comprising:
   a container configured to contain biopharmaceutical materials therein;
   a holder having a cradle bounding a cavity, said container received in said cavity;
   said holder comprising a first portion and a second portion forming said cradle, said container received between said first portion and said second portion to connect said container to said holder; and
   a support member protruding from an outer surface of said cradle, said member structurally supporting said cradle and inhibiting deformation of said cradle in response to an expansion of biopharmaceutical material held in said container due to freezing;
   said support member having opposite ends thereof directly connected to a first portion of an outer rim and a second portion of said outer rim, said outer rim connected to said cradle and extending around a perimeter of said cradle, said first portion and said second portion located on opposite sides of said holder relative to each other along said perimeter.

15. The system of claim 14 wherein said cradle comprises an outer cradle surface, said outer cradle surface being recessed toward said container relative to an outermost surface of said outer rim such that said outermost surface is located further from said second portion than said outer cradle surface is located from said second portion.

16. The system of claim 14 wherein said cradle comprises a bottom having an inner surface facing said cavity receiving said container and opposite said outer surface, said cradle comprising a groove in said inner surface corresponding to said support member protruding from said outer surface.

17. A system for use in freezing, storing and thawing biopharmaceutical materials, said system comprising:
   a container configured to contain biopharmaceutical materials therein;
   a holder having a cavity, said container received in said cavity;

said holder comprising a first portion and a second portion, said container received between said first portion and said second portion to connect said container to said holder;

said first portion comprising a first bottom bounding said cavity and said second portion comprising a second bottom bounding said cavity, said first bottom and said second bottom opposite said cavity relative to each other and moveable apart from each other in response to the biopharmaceutical material within said container and said cavity freezing and expanding;

wherein the first bottom and the second bottom are configured to move away from each other due to the freezing such that outer surfaces of the first bottom and the second bottom do not extend beyond an outer rim of the holder in a direction one of from said first portion toward said second portion and from said second portion toward said first portion, said outer rim connected to said first portion, and said first portion and said second portion connected to each other such that said first bottom and said second bottom are moveable away from each other while a remainder of said first portion and a second remainder of said second portion avoid moving relative to each other; and said first portion comprising an inner rim extending completely around a perimeter of said container, said inner rim comprising longitudinal sides, ends, and curved corners surrounding said perimeter, each of said corners connecting a longitudinal side of said longitudinal sides to an end of said ends, said container contacting said bottom, edges, and at least one corner of said corners;

said edges extending from said bottom and extending entirely around said perimeter of said cavity, said edges comprising a plurality of curved surfaces, each curved surface of said plurality of curved surfaces forming arcs having respective axes passing through said cavity, said container contacting said plurality of curved surfaces.

18. The system of claim 17 wherein said first bottom and said second bottom curve inwardly toward each other.

19. The system of claim 1 further comprising a second cavity between said cradle and said outer rim, said second cavity being isolated from said container, said second cavity extending around said perimeter of said container.

20. The system of claim 1 wherein said outer rim extends around a perimeter of said container.

21. The system of claim 14 wherein said biopharmaceutical materials comprise liquid biopharmaceutical materials.

22. The system of claim 17 wherein said biopharmaceutical materials comprise liquid biopharmaceutical materials.

23. A system for use in freezing, storing and thawing biopharmaceutical materials, said system comprising:

a container configured to contain biopharmaceutical materials therein;

a holder having a cradle bounding a cavity, said container received in said cavity;

said holder comprising a first portion and a second portion forming said cradle, said container received between said first portion and said second portion to connect said container to said holder;

said first portion comprising a first bottom connected to first edges extending from said first bottom toward said second portion and extending entirely around a perimeter of said cavity;

said second portion comprising a second bottom opposite said cavity relative to said first bottom, said second bottom connected to second edges extending from said second bottom toward said first portion and extending entirely around said perimeter of said cavity;

said first edges and said second edges comprising a plurality of curved surfaces, each curved surface of said plurality of curved surfaces forming an arc having an axis in said cavity, said container contacting said plurality of curved surfaces;

said first portion comprising an outer rim connected to said cradle and extending around said first portion;

said cradle comprising an outer cradle surface, said outer cradle surface being recessed toward said container relative to an outermost rim surface of said outer rim such that said outermost surface is located further from said second portion than said outer cradle surface is located away from said second portion; and said outer rim comprising a first plurality of outer teeth extending away from said container, said outer teeth engageable with a second plurality of outer teeth of a second outer rim of a second holder to stack said holder and said second holder and to inhibit movement between said holder and said second holder.

24. The system of claim 23 wherein said first portion comprises an inner rim, said second portion comprises a second inner rim, said inner rim comprising a first plurality of inner teeth and said second inner rim comprising a second plurality of inner teeth, said first plurality of inner teeth and said second plurality of inner teeth engageable with each other to connect said first inner rim to said second inner rim.

25. The system of claim 23 wherein said second portion comprises a second outer rim connected to said cradle, said second outer rim comprising a third plurality of teeth engageable with a fourth plurality of teeth of a third holder to stack said holder and said third holder and to inhibit movement between said holder and said third holder.

26. The system of claim 25 wherein said biopharmaceutical materials comprise liquid biopharmaceutical materials.

* * * * *